United States Patent
Yamada et al.

(10) Patent No.: US 7,181,840 B2
(45) Date of Patent: Feb. 27, 2007

(54) METHOD OF MANUFACTURING A GAS SENSOR

(75) Inventors: Hirokazu Yamada, Nagoya (JP); Masato Ozawa, Toyota (JP)

(73) Assignee: Denso Corporation (JP)

( * ) Notice: Subject to any disclaimer, the term of this patent is extended or adjusted under 35 U.S.C. 154(b) by 244 days.

(21) Appl. No.: 10/916,501

(22) Filed: Aug. 12, 2004

(65) Prior Publication Data

US 2005/0011063 A1    Jan. 20, 2005

Related U.S. Application Data

(62) Division of application No. 09/960,736, filed on Sep. 24, 2001, now Pat. No. 6,792,678.

(30) Foreign Application Priority Data

| Sep. 29, 2000 | (JP) | ............................. 2000-300538 |
| Jul. 27, 2001 | (JP) | ............................. 2001-228204 |

(51) Int. Cl.
*H01R 43/00* (2006.01)

(52) U.S. Cl. .................. 29/857; 29/593; 29/592.1; 29/595; 73/23.31; 73/31.05; 204/424; 204/428; 219/121.64

(58) Field of Classification Search .................. 29/204, 29/509–511, 592.1, 593–595, 609.1, 857; 29/860; 73/23.31, 23.32, 31.05; 204/424, 204/429, 428; 219/121.64; 228/175, 178, 228/184

See application file for complete search history.

(56) References Cited

U.S. PATENT DOCUMENTS

| 4,556,475 A | 12/1985 | Bayha et al. |
| 4,560,463 A | 12/1985 | Frey et al. |
| 4,597,849 A * | 7/1986 | Burkhardt et al. ........ 174/77 R |
| 4,730,389 A | 3/1988 | Baudino et al. |
| 4,987,519 A | 1/1991 | Hutchins et al. |
| 5,139,696 A | 8/1992 | Frechet et al. |
| 5,573,650 A | 11/1996 | Fukaya et al. |
| 6,039,856 A | 3/2000 | Weyl et al. |
| 6,360,581 B1 * | 3/2002 | Murase et al. ............. 73/31.05 |
| 6,415,647 B1 * | 7/2002 | Yamada et al. ............ 73/31.05 |

FOREIGN PATENT DOCUMENTS

| JP | 2847418 | 11/1998 |
| JP | 11-242013 | 9/1999 |

* cited by examiner

*Primary Examiner*—Minh Trinh
*Assistant Examiner*—Donghai D. Nguyen
(74) *Attorney, Agent, or Firm*—Nixon & Vanderhye PC

(57) ABSTRACT

An improved manufacturing method for a gas sensor is provided which is capable of establishing a required hermetic seal in a body of the gas sensor. The method includes preparing a sensor assembly including a housing, an air cover, an insulation porcelain, and a sensor element, pressing the air cover against the housing to fit an end of the air cover on an end of the housing to form an overlap thereof, and welding the air cover to the housing over the overlap. The welding is accomplished while pressing the air cover against the housing, thereby compressing an elastic member in the air cover to establish a hermetic seal between the sensor element and the housing.

6 Claims, 8 Drawing Sheets

METHOD OF MANUFACTURING A GAS SENSOR

This application is a division of application No. 09/960,736, filed Sep. 24, 2001, now U.S. Pat. No. 6,792,678, the entire contents of which is hereby incorporated by reference in this application.

BACKGROUND OF THE INVENTION

1. Technical Field of the Invention

The present invention relates generally to a manufacturing method of a gas sensor which may be used in air-fuel ratio control of automotive internal combustion engines and a manufacturing machine therefore, and more particularly to a manufacturing method and machine for such a gas sensor which is capable of establishing a hermetic seal in the gas sensor reliably.

2. Background Art

Japanese Patent Publication No. 2847418 discloses a typical gas sensor used to measure an oxygen content of exhaust gasses of an automotive internal combustion engine. In this sensor, a cup or cover is joined to a sensor holder by staking, therefore, a sufficient degree of sealing between a sensor element and the atmosphere, i.e., the outside of the cover is not obtained.

SUMMARY OF THE INVENTION

It is therefore an object of the invention to provide an improved manufacturing system for a gas sensor which is capable of establishing a required hermetic seal in the gas sensor.

According to the first aspect of the invention, there is provided a gas sensor manufacturing method which comprise the steps of: (1) preparing an assembly which has a length and includes (a) a housing which has a length made up of a first end portion, a second end portion, and a flange between the first and second end portions, (b) a cover which is made up of a small-diameter portion, a large-diameter portion, and a shoulder formed between the small-diameter portion and the large-diameter portion, (c) a first insulation porcelain disposed in the large-diameter portion of the cover in contact with the shoulder through an elastic member, (d) a second insulation porcelain disposed in the housing in contact of an end thereof with an end of the first insulation porcelain in alignment with each other, and (e) a laminated sensor element disposed in the second insulation porcelain; (2) pressing the cover against the housing in a lengthwise direction of the assembly to fit an end of the large-diameter portion of the cover on the first end portion of the housing to form an overlap; (3) tacking the large-diameter portion of the cover to the first end portion of the housing at the overlap while pressing the cover against the housing; (4) rotating the assembly about the length thereof; and (5) welding the large-diameter portion of the cover to the first end portion of the housing over the overlap.

In the preferred mode of the invention, the pressing steps presses the cover against the housing while compressing the elastic member to urge the second insulation porcelain against an inner wall of the housing elastically to establish a hermetic seal between an outer wall of the second insulation porcelain and the inner wall of the housing.

The welding step is performed while pressing the cover against the housing.

The pressure exerted on the cover may alternatively be released after the tacking step.

The welding step is performed by laser welding.

The tacking step makes at least two tack welds in the overlap of the cover and the housing.

According to the second aspect of the invention, there is provided a gas sensor manufacturing method which comprises the steps of: (1) preparing an assembly which has a length and includes (a) a housing which has a length made up of a first end portion, a second end portion, and a flange between the first and second end portions, (b) a cover which is made up of a small-diameter portion, a large-diameter portion, and a shoulder formed between the small-diameter portion and the large-diameter portion, and (c) an insulation porcelain disposed in the large-diameter portion of the cover in contact with the shoulder through an elastic member, (d) a cup-shaped sensor element disposed in the housing; (2) pressing the cover against the housing in a lengthwise direction of the assembly to fit an end of the large-diameter portion of the cover on the first end portion of the housing to form an overlap; (3) tacking the large-diameter portion of the cover to the first end portion of the housing at the overlap while pressing the cover against the housing; (4) rotating the assembly about the length thereof; and (5) welding the large-diameter portion of the cover to the first end portion of the housing over the overlap.

In the preferred mode of the invention, the pressing steps presses the cover against the housing while compressing the elastic member to urge the sensor element against an inner wall of the housing elastically to establish a hermetic seal between an outer wall of the sensor element and the inner wall of the housing.

The welding step is performed while pressing the cover against the housing.

The pressure exerted on the cover may alternatively be released after the tacking step.

The welding step is performed by laser welding.

The tacking step makes at least two tack welds in the overlap of the cover and the housing.

According to the third aspect of the invention, there is provided a gas sensor manufacturing method which comprises the steps of: (1) preparing an assembly which has a length and includes (a) a housing which has a length made up of a first end portion, a second end portion, and a flange between the first and second end portions, (b) a cover which is made up of a small-diameter portion, a large-diameter portion, and a shoulder formed between the small-diameter portion and the large-diameter portion, (c) a first insulation porcelain disposed in the large-diameter portion of the cover in contact with the shoulder through an elastic member, (d) a second insulation porcelain disposed in the housing in contact of an end thereof with an end of the first insulation porcelain in alignment with each other, and (e) a laminated sensor element disposed in the second insulation porcelain; (2) pressing the cover against the housing in a lengthwise direction of the assembly to fit an end of the large-diameter portion of the cover on the first end portion of the housing to form an overlap; and (3) welding the large-diameter portion of the cover to the first end portion of the housing at the overlap while pressing the cover against the housing.

In the preferred mode of the invention, the pressing steps presses the cover against the housing while compressing the elastic member to urge the second insulation porcelain against an inner wall of the housing elastically to establish a hermetic seal between an outer wall of the second insulation porcelain and the inner wall of the housing.

The welding step is performed while rotating the cover and the housing.

The welding step may alternatively be performed while fixing the cover and the housing.

The welding step welds the large-diameter portion of the cover to the first end portion of the housing around an overall periphery of the overlap through laser welding.

According to the fourth aspect of the invention, there is provided a gas sensor manufacturing method which comprises the steps of: (1) preparing an assembly which has a length and includes (a) a housing which has a length made up of a first end portion, a second end portion, and a flange between the first and second end portions, (b) a cover which is made up of a small-diameter portion, a large-diameter portion, and a shoulder formed between the small-diameter portion and the large-diameter portion, and (c) an insulation porcelain disposed in the large-diameter portion of the cover in contact with the shoulder through an elastic member, (d) a cup-shaped sensor element disposed in the housing; (2) pressing the cover against the housing in a lengthwise direction of the assembly to fit an end of the large-diameter portion of the cover on the first end portion of the housing to form an overlap; and (3) welding the large-diameter portion of the cover to the first end portion of the housing at the overlap while pressing the cover against the housing.

In the preferred mode of the invention, the welding step is performed while rotating the cover and the housing.

The welding step may alternatively be performed while fixing the cover and the housing.

The welding step welds the large-diameter portion of the cover to the first end portion of the housing around an overall periphery of the overlap through laser welding.

According to the fifth aspect of the invention, there is provided a gas sensor manufacturing method which comprise the steps of: (1) preparing an assembly which has a length and includes (a) a housing which has a length made up of a first end portion, a second end portion, and a flange between the first and second end portions, (b) a cover which is made up of a small-diameter portion, a large-diameter portion, and a shoulder formed between the small-diameter portion and the large-diameter portion, (c) a first insulation porcelain disposed in the large-diameter portion of the cover in contact with the shoulder through an elastic member, (d) a second insulation porcelain disposed in the housing in contact of an end thereof with an end of the first insulation porcelain in alignment with each other, and (e) a laminated sensor element disposed in the second insulation porcelain; (2) pressing the cover against the housing in a lengthwise direction of the assembly until a pressure exerted on the housing reaches a given pressure level to fit an end of the large-diameter portion of the cover on the first end portion of the housing to form an overlap; and (3) welding the large-diameter portion of the cover to the first end portion of the housing at the overlap while pressing the cover against the housing.

In the preferred mode of the invention, the pressing steps presses the cover against the housing while compressing the elastic member to urge the second insulation porcelain against an inner wall of the housing elastically to establish a hermetic seal between an outer wall of the second insulation porcelain and the inner wall of the housing.

The given pressure level is 1.2 times greater than or equal to an elastic pressure produced by the elastic member.

According to the sixth aspect of the invention, there is provided a manufacturing method which comprise the steps of: (1) preparing an assembly which has a length and includes (a) a housing which has a length made up of a first end portion, a second end portion, and a flange between the first and second end portions, (b) a cover which is made up of a small-diameter portion, a large-diameter portion, and a shoulder formed between the small-diameter portion and the large-diameter portion, and (c) an insulation porcelain disposed in the large-diameter portion of the cover in contact with the shoulder through an elastic member, (d) a cup-shaped sensor element disposed in the housing; (2) pressing the cover against the housing in a lengthwise direction of the assembly until a pressure exerted on the housing reaches a given pressure level to fit an end of the large-diameter portion of the cover on the first end portion of the housing to form an overlap; and (3) welding the large-diameter portion of the cover to the first end portion of the housing at the overlap while pressing the cover against the housing.

In the preferred mode of the invention, the pressing steps presses the cover against the housing while compressing the elastic member to urge the sensor element against an inner wall of the housing elastically to establish a hermetic seal between an outer wall of the sensor element and the inner wall of the housing.

The given pressure level is 1.2 times greater than or equal to an elastic pressure produced by the elastic member.

According to the seventh aspect of the invention, there is provided a gas sensor manufacturing machine designed to produce a gas sensor using an assembly which has a length and includes (a) a housing which has a length made up of a first end portion, a second end portion, and a flange between the first and second end portions, (b) a cover which is made up of a small-diameter portion, a large-diameter portion, and a shoulder formed between the small-diameter portion and the large-diameter portion, (c) a first insulation porcelain disposed in the large-diameter portion of the cover in contact with the shoulder through an elastic member, (d) a second insulation porcelain disposed in the housing in contact of an end thereof with an end of the first insulation porcelain in alignment with each other, and (e) a laminated sensor element disposed in the second insulation porcelain. The machine comprises: (1) a first annular press plate fitted on the first end portion of the housing in engagement with the flange; (2) a second annular press plate fitted on the small-diameter portion of the cover in engagement with the shoulder of the cover; and (3) a pressing means for pressing the cover against the housing in a lengthwise direction of the assembly to fit an end of the large-diameter portion of the cover on the first end portion of the housing to form an overlap; (4) a tacking means for tacking the large-diameter portion of the cover to the first end portion of the housing at the overlap while pressing the cover against the housing; (5) a rotating means for rotating the assembly; and (6) a welding means for welding the large-diameter portion of the cover to the first end portion of the housing over the overlap.

In the preferred mode of the invention, the tacking means and the welding means are implemented by a welding machine including welding heads which are rotatable around the overlap.

According to the eighth aspect of the invention, there is provided a gas sensor manufacturing machine designed to produce a as sensor using an assembly which has a length and includes (a) a housing which has a length made up of a first end portion, a second end portion, and a flange between the first and second end portions, (b) a cover which is made up of a small-diameter portion, a large-diameter portion, and a shoulder formed between the small-diameter portion and the large-diameter portion, and (c) an insulation porcelain disposed in the large-diameter portion of the cover in contact with the shoulder through an elastic member, (d) a cup-shaped sensor element disposed in the housing. The machine comprises: (1) a first annular press plate fitted on the first end portion of the housing in engagement with the flange; (2) a second annular press plate fitted on the small-diameter portion of the cover in engagement with the shoulder of the cover; (3) a pressing means for pressing the cover against the housing in a lengthwise direction of the assembly to fit an end of the large-diameter portion of the cover on the first end portion of the housing to form an overlap; (4) a tacking means for tacking the large-diameter portion of the cover to the first end portion of the housing at the overlap while pressing the cover against the housing; (5) a rotating means for rotating the assembly, and (6) a welding means for welding the large-diameter portion of the cover to the first end portion of the housing over the overlap.

In the preferred mode of the invention, the tacking means and the welding means are implemented by a welding machine including welding heads which are rotatable around the overlap.

BRIEF DESPCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

DESCRIPTION OF THE PREFERRED EMBODIMENTS

Figure 1:
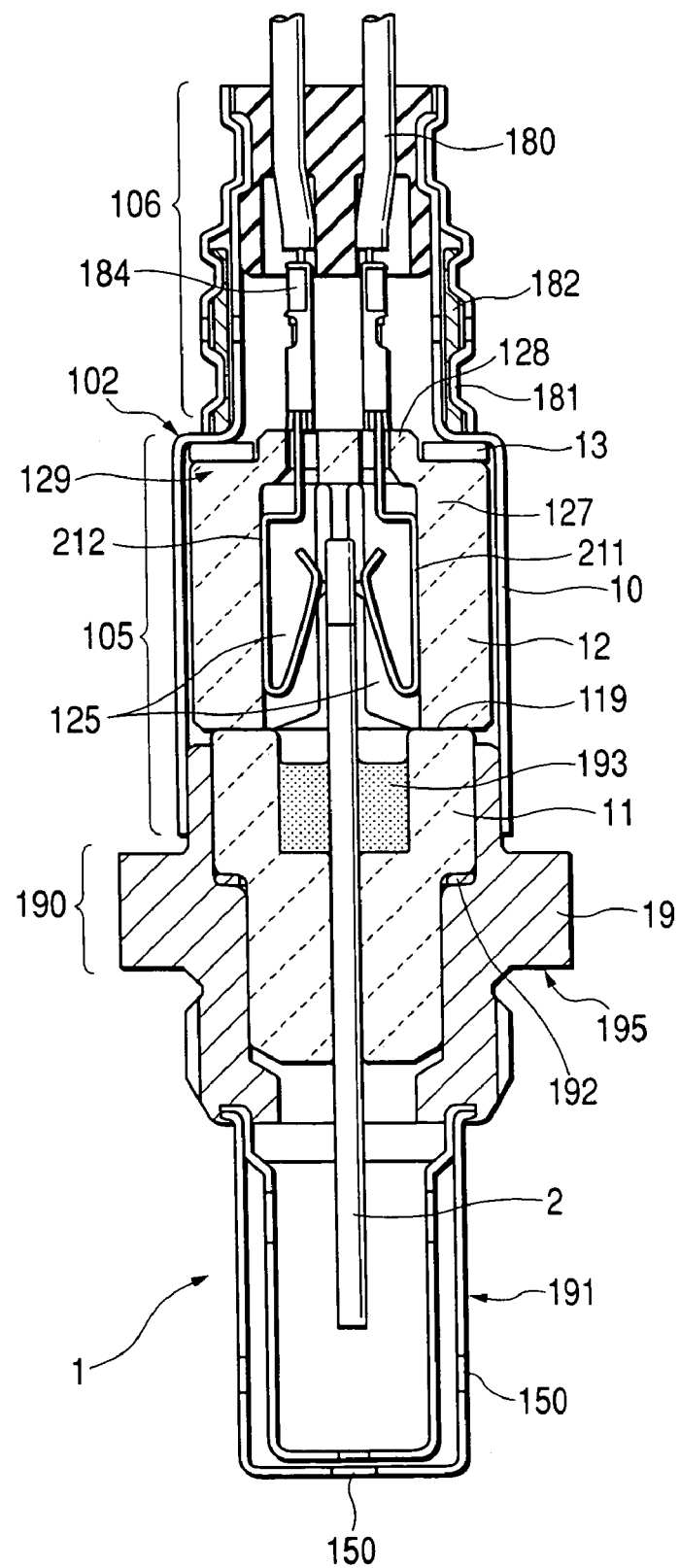
FIG. 1 is a longitudinal sectional view which shows a laminated sensor element-equipped gas sensor to be manufactured by a method provided by the invention.

Referring to the drawings, wherein like reference numbers refer to like parts in several views, particularly to FIG. 1, there is shown a gas sensor 1 according to the first embodiment of the invention which may be employed in a burning control system or air-fuel ratio control system of an automotive vehicle to measure concentrations of components such as NOx, CO, HC, and $O_2$ contained in exhaust gasses of the engine.

The gas sensor 1 generally includes a sensor element 2, a first insulation porcelain 12, a second insulation porcelain 11, a hollow cylindrical housing 19, and an air cover 10. The sensor element 2 is made of a laminated plate consisting of a solid electrolyte body, ceramic layers, and electrode layers. For example, U.S. Pat. No. 5,573,650, issued on Nov. 12, 1996 to Fukaya et al. teaches a typical laminated sensor element, disclosure of which is incorporated herein by reference. The second insulation porcelain 11 is made of a hollow cylindrical member and is fitted within the housing 19 and holds therein the sensor element 2. The first insulation porcelain 12 is mounted on the second insulation porcelain 11 in alignment with each other and surrounds a base portion of the sensor element 2.

The housing 19 has a large-diameter portion or flange 190. The air cover 10 is fitted at an end thereof on a small-diameter portion (also referred to as a base end portion below) of the housing 19 to cover the first insulation porcelain 12. The gas sensor 1 also includes a protective cover assembly 191 consisting of an outer cover and an inner cover. The protective cover assembly 191 is installed on a head of the housing 19 to define a gas chamber into which a gas to be measured is admitted through gas holes 150 formed in the outer and inner covers.

The air cover 10 is made up of a large-diameter portion 105 greater in diameter than the first insulation porcelain 12, a small-diameter portion 106 smaller in diameter than the first insulation porcelain 12 and a shoulder 102 between the large-diameter portion 105 and the small-diameter portion 106.

The first insulation porcelain 12 is made of a hollow cylindrical insulating member and retained between an upper end, as viewed in FIG. 1, of the second insulation porcelain 11 and the shoulder 102 of the air cover 10. Between an inner wall of the shoulder 102 and a base end 129 of the first insulation porcelain 12, an annular elastic ring 13 made of a conical spring is disposed to urge the first insulation porcelain 12 into firm engagement with the second insulation porcelain 11, thereby establishing a hermetic seal in a gap between the second insulation porcelain 11 and the housing 19.

The assembling of the gas sensor 1 will be described below in brief.

Figure 4:
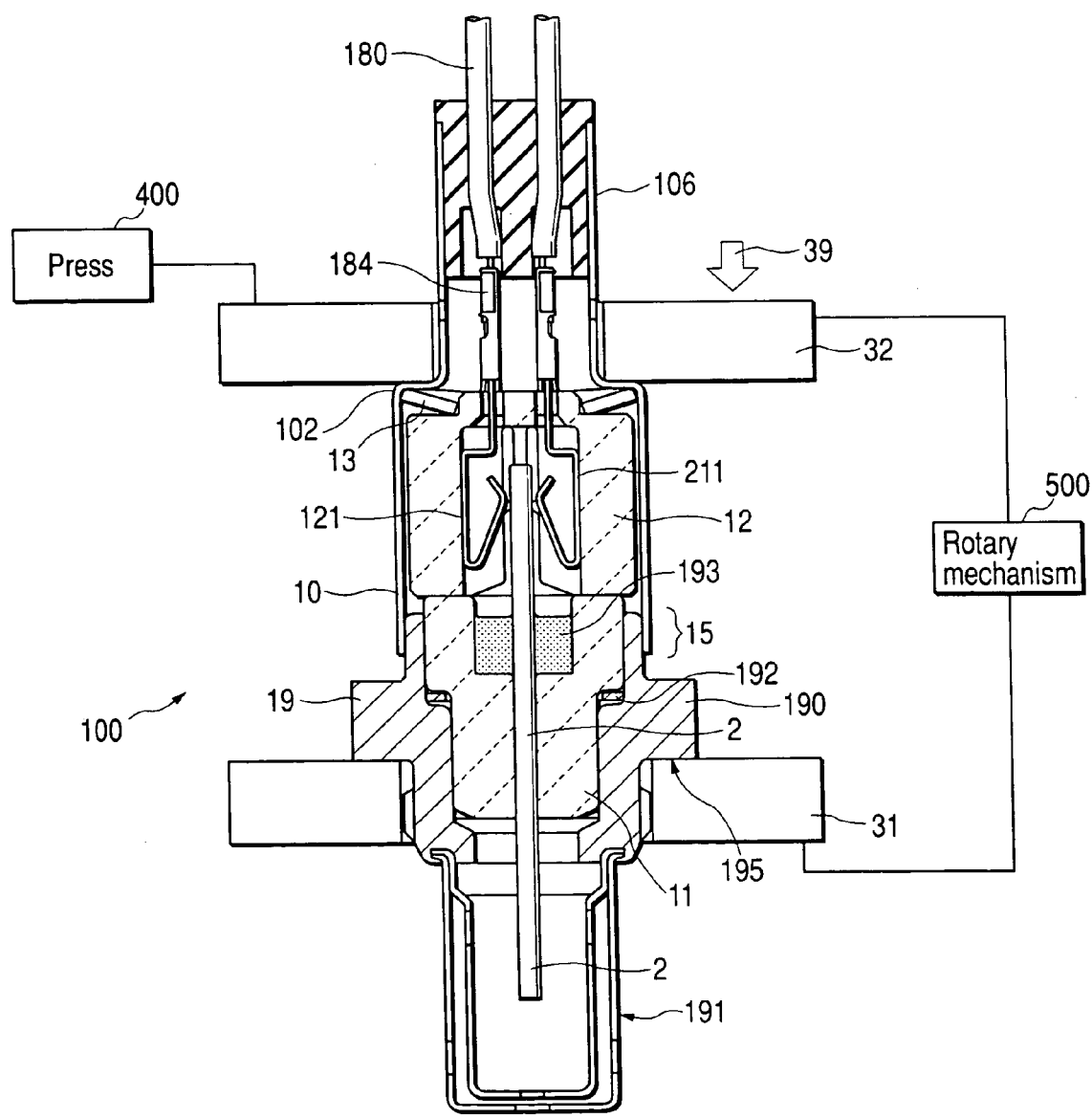
FIG. 4 is a sectional view which shows the process of pressing the sensor assembly of FIG. 3 for welding an air cover to a housing securely.

First, an assembly 100 having a given length made up of the air cover 10, the elastic ring 13, the first insulation porcelain 12, the sensor element 2, the second insulation porcelain 11, the housing 19, and the protective cover assembly 191 is, as shown in FIG. 4, prepared. The fabrication of the assembly 100 will be described later in detail.

A manufacturing machine used in producing the gas sensor 1 includes an annular head plate 31, an annular base plate 32 which are, as clearly shown in FIG. 4, laid in parallel, a press mechanism 400, and a rotary mechanism 500.

After the assembly 100 is prepared, the annular head plate 31 is fitted on the head of the housing 19 in surface contact with an end surface of the flange 190. The annular base plate 32 is fitted on the small-diameter portion 106 of the air cover 10 in surface contact with the shoulder 102. Next, the annular head plate 31 and the annular base plate 32 are pressed by the press mechanism 400 in approach directions to fit the base end portion of the housing 19 into the end of the air cover 10 until a given overlap 15 is formed. The air cover 10 and the housing 19 are tacked, as described later in detail, at the overlap 15 while they are being pressed. The press mechanism 400 may be implemented by a known press machine using, for example, hydraulic cylinders. The structure itself is not essential part of the invention, and explanation thereof in detail will be omitted here.

The assembly 100 is rotated about a longitudinal center line thereof by the rotary mechanism 500 which may be implemented by a known structure consisting of a gear set and an electric motor (not shown). The end of the air cover 10 is welded at an overall periphery of the overlap 15 to the base end portion of the housing 19. The assembly 100 is preferably kept pressed y the annular head plate 31 and the annular base plate 32 during the welding of the air cover 10, thereby minimizing a positional shift between the air cover 10 and the housing 19.

Referring back to FIG. 1, the air cover 10 is, as described above, mounted on the base end portion of the housing 19. An outer air cover 181 is provided around the air cover 10 and staked or crimped to retain a water-repellent filter 182 on the small-diameter portion 106 of the air cover 10.

The second insulation porcelain 11 is retained within the housing 19 hermetically through a metallic packing ring 192 placed on an annular tapered shoulder formed on an inner wall of the housing 19 and holds therein the sensor element 2 through a glass sealing member 193.

The first insulation porcelain 12 is, as described above, mounted directly on the base end 119 of the second insulation porcelain 11 and surrounded by the air cover 10. The elastic ring 13 is disposed between the shoulder 102 and the annular base end 129 of the first insulation porcelain 12 to elastically urge the first insulation porcelain 12 into constant engagement with the second insulation porcelain 11. The annular base end 129 of the first insulation porcelain 12 is formed around a cylindrical projecting part or boss 128 on the end wall of the hollow cylindrical body 127. The elastic ring 13 is, as described above, made of a conical spring and placed on the base end 129 of the first insulation porcelain 12 with the periphery thereof, as clearly shown in FIG. 4, oriented upward before the first insulation porcelain 12 is inserted into the air cover 10 in the assembling process.

The first insulation porcelain 12 has disposed therein two pairs of leads 211 and 212 (only two are shown for the simplicity of illustration) each of which is made of a metal wire folded elastically to make an electric contact at one end with an electrode terminal (not shown) formed on the sensor element 2. The leads 211 and 212 extend at the other end through holes formed in the boss 128 of the first insulation porcelain 12 and connect with four leads 180 through connectors 184, respectively, for transmission of sensor signals between the sensor element 2 and an external device and supply of electric power to a heater installed on the sensor element 2.

The first insulation porcelain 12 has four vertical ribs 125 formed on an inner wall thereof at regular intervals. Between adjacent two of the vertical ribs 125, each of the leads 211 and 212 is retained and insulated from the adjacent ones.

The assembling of the gas sensor 1 will be described bellow in detail.

First, the assembly 100 is prepared in the following steps.

Figure 2:
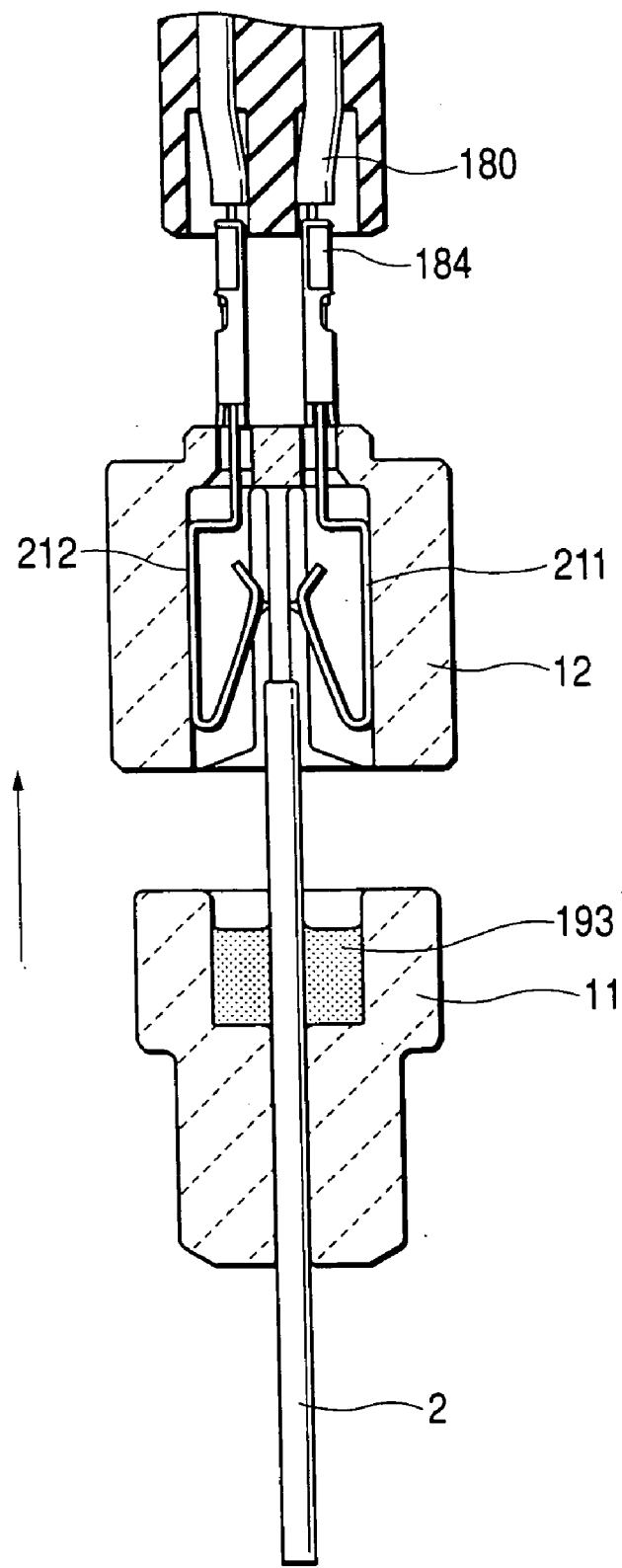
FIG. 2 is a partially sectional view which shows the process of making a sensor assembly.

The sensor element 2 is, as clearly shown in FIG. 2, inserted into the second insulation porcelain 11. The glass sealing member 193 is fitted in the chamber of the second insulation porcelain 11 to establish a hermetic seal between the sensor element 2 and the second insulation porcelain 11. The glass sealing member 193 also serves to retain the sensor element 2 within the second insulation porcelain 11 rigidly.

The leads 211 and 212 connecting with the leads 180 through the connectors 184 are installed in the first insulation porcelain 12. The base portion of the sensor element 2 is inserted into the first insulation porcelain 12 to establish an electric connection the electrodes formed on the sensor element 2 with the leads 211 and 212. The leads 211 and 212 are, as described above, made of a spring member and thus hold the base portion of the sensor element 2 elastically within the first insulation porcelain 12.

Figure 3:
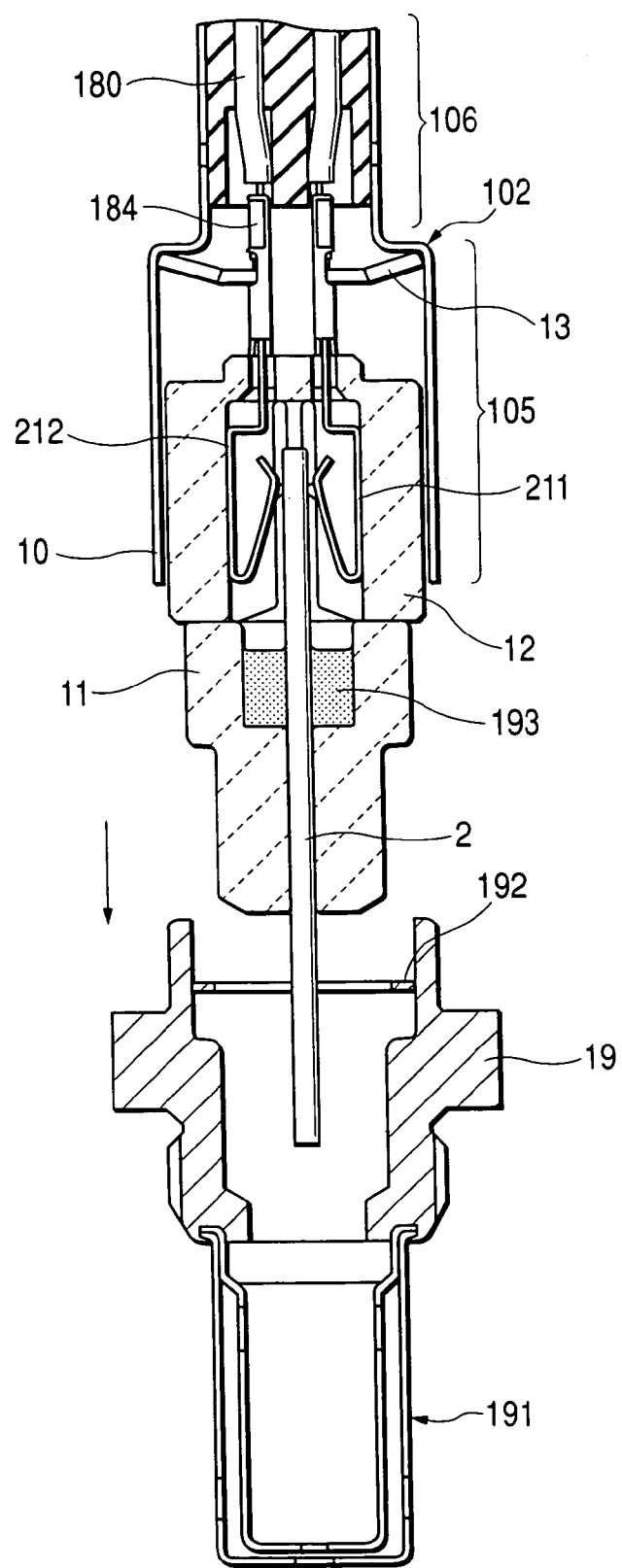
FIG. 3 is a sectional view which shows the process of inserting an insulation porcelain into a housing to form a sensor assembly.

Next, the protective cover assembly 191 is, as clearly shown in FIG. 3, installed in the end of the housing 19 by staking. The metallic packing ring 192 is placed on the inner shoulder of the housing 19. The elastic ring 13 is put in the air cover 10. The air cover 10 is then put on the first insulation porcelain 12 and moved downward, as indicated by an arrow in FIG. 3, without compressing the metal packing ring 192 tightly, thereby inserting the second insulation porcelain 11 into the housing 19 to complete the assembly 100. In the assembly 100, the metal packing ring 192 does not yet establish a hermetic seal between the second insulation porcelain 11 and the housing 19. The elastic ring 13 is not pressed sufficiently to exert the elastic pressure on the base end 129 of the first insulation porcelain 12 . Specifically, the elastic ring 13 is, as can be seen in FIG. 3, oriented at the periphery thereof upward.

After the assembly 100 is prepared, the annular head plate 31 is, as described above in FIG. 4, fitted on the head of the housing 19 into contact with an end wall 195 of the flange 190 and then retained firmly in the manufacturing machine. Next, the annular base plate 32 is fitted on the small-diameter portion 106 of the air cover 10 and moved downward, as viewed in FIG. 4, by the press mechanism 400 at a given high speed into contact with the shoulder 102.

After hitting on the shoulder 102 of the air cover 10, the annular base plate 32 is moved at a decreased speed and pushed downward to exert the pressure 39 on the shoulder 102 of the air cover 10 until the pressure 39 reaches about 650 kg. This causes the base end portion of the housing 19 to be forced into the end of the air cover 10, thereby forming the overlap 15 and the elastic ring 13 to be flattened, thereby exerting the elastic pressure on the first insulation porcelain 12 downward in a longitudinal direction of the assembly 100. The metal packing ring 192 is also compressed to hermetically seal a gap between the second insulation porcelain 11 (i.e., the sensor element 2) and the housing 19. It is advisable that the pressure 39 be 1.2 times greater than the elastic pressure produced by the elastic ring 13 in order to force the housing 19 into the open end of the housing 19 reliably and to compress the metal packing ring 192 through the first insulation porcelain 11 for increasing the adhesion of the metal packing ring 192 to the surfaces of the first insulation porcelain 11 and the housing 19 to form a hermetic seal between the first insulation porcelain 11 and the housing 19 and lower than 7.8 kN in order to avoid the breakage of the first and second insulation porcelain 11 and 12.

The assembly 100 is held under a pressure of 650 kg.

Figure 5:
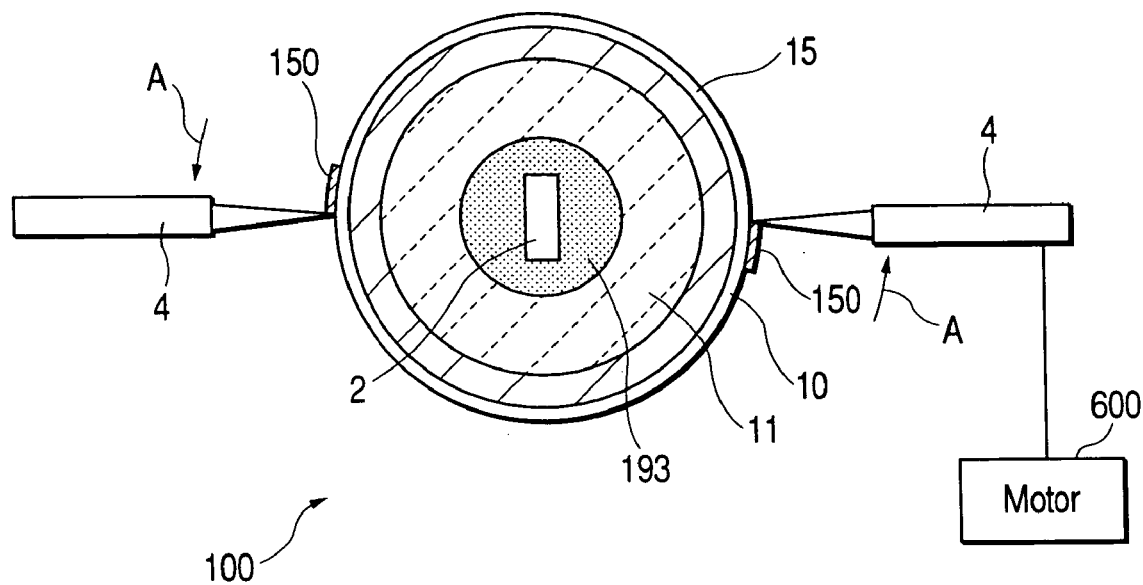
FIG. 5 is a horizontal sectional view which shows welding heads placed around the gas assembly of FIG. 3 to join an air cover to a housing.

Two welding heads 4, as shown in FIG. 5, are placed around the overlap 15 of the air cover 10 and the housing 19 and opposed diametrically to each other. Next, the welding heads 4 are turned together in a direction, as indicated by an arrow A, by an electric motor 600 to make two tack welds or joints 150 in the overlap 15. Each of the joints 150 extends in a circumferential direction of the overlap 15 and has a length of 7 mm. The joints 150 are formed at radially symmetrical positions with respect to the center of the assembly 100. A single joint 150 may be formed in the overlap, but however, at least two joints 150 are preferable in order to maintain the positional relation between the air cover 10 and the housing 19. The joints 150 may alternatively be provided by spot welds. Additionally, the diameter of the open end of the air cover 10 is preferably smaller than that of the base end portion of the housing 19. Specifically, it is advisable that the base end portion of the housing 19 be press fit in the open end of the air cover 10 in order to avoid an undesirable lift of the air cover 10 from the housing 19 during the tacking.

The welding heads 4 are connected to a typical laser welding machine (not shown) and emit laser beams to the overlap 15.

After the air cover 10 and the housing 19 are joined by the laser welding, the pressure exerted on the assembly 100 is decreased down to 10 kg. The assembly 100 is turned up to a speed of 1500 mm/minute. The welding heads 4 are, like the above, placed around the overlap 15 again and held stationary. Laser beams are radiated from the welding heads 4 to weld the air over 10 to the housing 19 over the whole of the periphery of the overlap 15.

The assembly 100 is stopped from rotating. The annular base plate 32 is removed from the shoulder 102 of the air cover 10. The assembly 100 is removed from the annular head plate 21.

Finally, the outer air cover 182 is fitted on the small-diameter portion 106 of the air cover 10 through the water-repellent filter 182 and pressed or crimped radially to join the outer air cover 182 to the air cover 10 firmly.

As described above, the air cover 10 and the housing 19 are tacked at the overlap 15, after which they are welded over the periphery of the overlap 15 to join the air cover 10 to the housing 19 completely. The tack welding serves to secure a desired positional relation between the air cover 10 and the housing 19, thus avoiding any shift between the air cover 10 and the housing 19 in the circumferential direction.

The tack welding is performed while the pressure is being exerted on the assembly 100 through the annular head and base plates 31 and 32, thus causing the elastic ring 13 to be flattened and held between the shoulder 102 of the air cover 20 and the base end 129 of the first insulation porcelain 12, which results production of pressure great enough to deform the metal packing ring 192 for sealing the gap between the outer wall of the second insulation porcelain 11 and the inner wall of the housing 19 hermetically.

The second embodiment will be described below which joins the air cover 10 and the housing 19 without making the tack welds.

The assembly 100 is prepared in the same manner as in the first embodiment. The annular head plate 31 is fitted on the head of the housing 19 into contact with the end wall 195 of the flange 190 and then retained firmly in the manufacturing machine. Next, the annular base plate 32 is fitted on the small-diameter portion 106 of the air cover 10 and moved downward, as viewed in FIG. 4, at a given high speed into contact with the shoulder 102.

After hitting on the shoulder 102 of the air cover 10, the annular base plate 32 is moved at a decreased speed and pushed downward to exert the pressure 39 on the shoulder 102 of the air cover 10 until the pressure 39 reaches about 650 kg. This causes the base end portion of the housing 19 to be forced into the end of the air cover 10, thereby forming the overlap 15 and the elastic ring 13 to be flattened, thereby exerting the elastic pressure on the first insulation porcelain 12 downward in a longitudinal direction of the assembly 100. The metal packing ring 192 is also compressed to hermetically seal a gap between the second insulation porcelain 11 (i.e., the sensor element 2) and the housing 19.

The assembly 100 is held under a pressure of 650 kg. The assembly 100 is turned up to a constant speed of 1500 mm/minute. The welding heads 4, as shown in FIG. 5, are placed around the overlap 15 of the air cover 10 and the housing 19 and opposed diametrically to each other. Laser beams are radiated from the welding heads 4 held stationary to weld the air over 10 to the housing 19 over the periphery of the overlap 15 of the rotating assembly 100.

After the air cover 10 and the housing 19 are joined by the laser welding, the rotation of the assembly 100 is stopped. The annular base plate 32 is removed from the shoulder 102 of the air cover 10. The assembly 100 is removed from the annular head plate 21.

Finally, the outer air cover 182 is fitted on the small-diameter portion 106 of the air cover 10 through the water-repellent filter 182 and pressed or crimped radially to join the outer air cover 182 to the air cover 10 firmly.

The third embodiment will be described below which turns the welding heads 4 to join the air cover 10 and the housing 19 without making the tack welds.

The assembly 100 is prepared in the same manner as in the first embodiment. The annular head plate 31 is fitted on the head of the housing 19 into contact with the end wall 195 of the flange 190 and then retained firmly in the manufacturing machine. Next, the annular base plate 32 is fitted on the small-diameter portion 106 of the air cover 10 and moved downward, as viewed in FIG. 4, at a given high speed into contact with the shoulder 102.

After hitting on the shoulder 102 of the air cover 10, the annular base plate 32 is moved at a decreased speed and pushed downward to exert the pressure 39 on the shoulder 102 of the air cover 10 until the pressure 39 reaches about 650 kg. This causes the base end portion of the housing 19 to be forced into the end of the air cover 10, thereby forming the overlap 15 and the elastic ring 13 to be flattened, thereby exerting the elastic pressure on the first insulation porcelain 12 downward in a longitudinal direction of the assembly 100. The metal packing ring 192 is also compressed to hermetically seal a gap between the second insulation porcelain 11 (i.e., the sensor element 2) and the housing 19.

The assembly 100 is held under a pressure of 650 kg. The welding heads 4, as shown in FIG. 5, are placed around the overlap 15 of the air cover 10 and the housing 19 and opposed diametrically to each other. The welding heads 4 are turned at a given speed. Laser beams are then radiated from the welding heads 4 to weld the air over 10 to the housing 19 over the periphery of the overlap 15 of the assembly 100 held stationary.

After the air cover 10 and the housing 19 are joined by the laser welding, the welding heads 4 are stopped from rotating. The annular base plate 32 is removed from the shoulder 102 of the air cover 10. The assembly 100 is removed from the annular head plate 21.

Finally, the outer air cover 182 is fitted on the small-diameter portion 106 of the air cover 10 through the water-repellent filter 182 and pressed or crimped radially to join the outer air cover 182 to the air cover 10 firmly.

Since the assembly 100 is held stationary, the pressure exerted on the assembly 100 is kept constant, thereby keeping the elastic ring 13 flat during the welding of the air cover 10 to the housing 19, which establishes a firm seal between the second insulation porcelain 11 and the housing 19.

Figure 6:
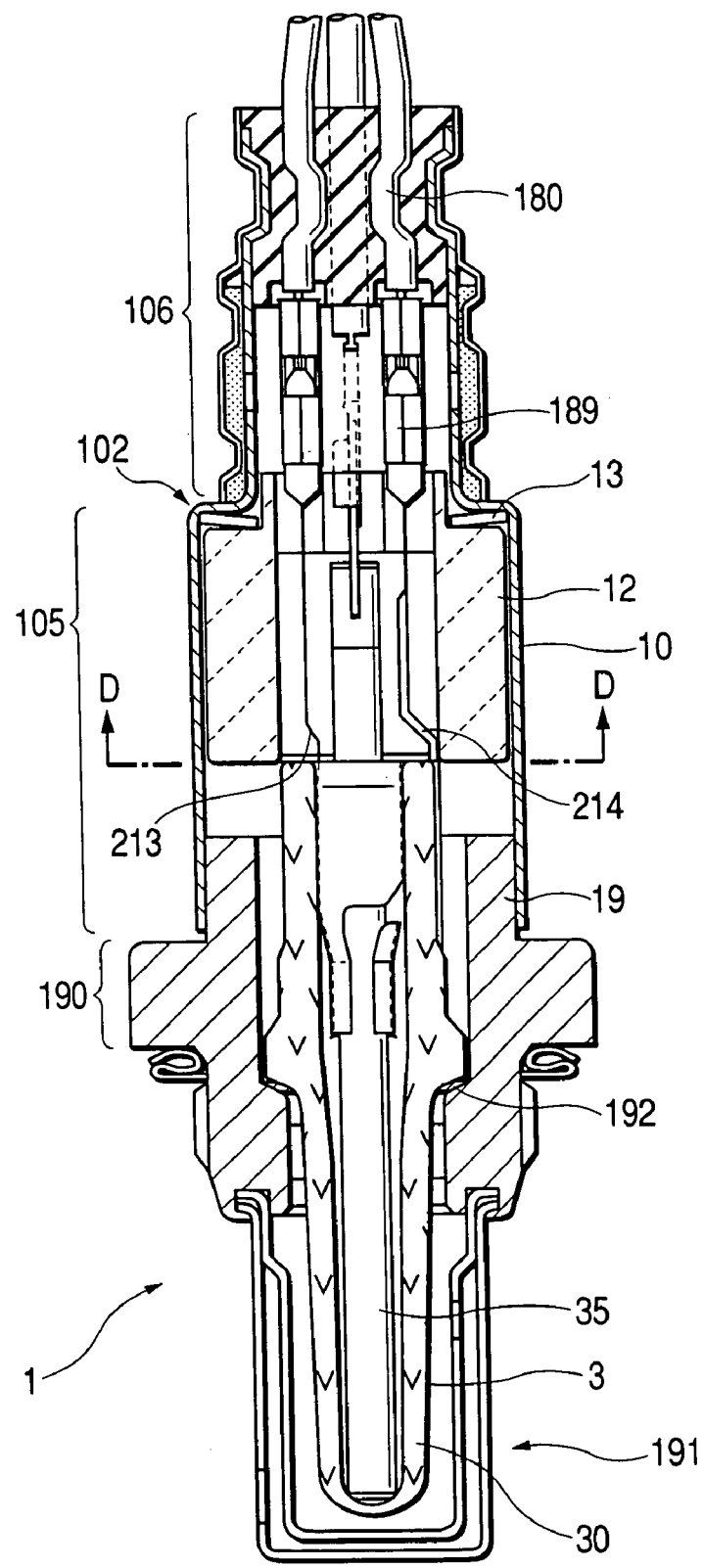
FIG. 6 is a longitudinal sectional view which shows a cup-shaped sensor element-equipped gas sensor to be manufactured by a method provided by the invention.

FIG. 6 shows a gas sensor 1 equipped with a cup-shaped sensor element 3.

The sensor element 3 consists of a cup-shaped solid electrolyte body 30 and a bar-shaped heater 35. The solid electrolyte body 30 is retained in a hollow cylindrical housing 19. The heater 35 is disposed within the solid electrolyte body 30. The housing 19, like the first embodiment, has the flange 190.

The sensor element 3 and the housing 19 are hermetically sealed by the packing ring 192 placed on an annular shoulder formed on an inner wall of the housing 19.

The solid electrolyte body 30 has a measuring electrode formed on an outer wall thereof and a reference gas electrode formed on an inner wall thereof. The gas measuring electrode and the reference gas electrode are known, for example, in European Patent Application EP 0918215 A2 assigned to the same assignee as that of this application, disclosure of which is incorporated herein by reference.

Figure 7:
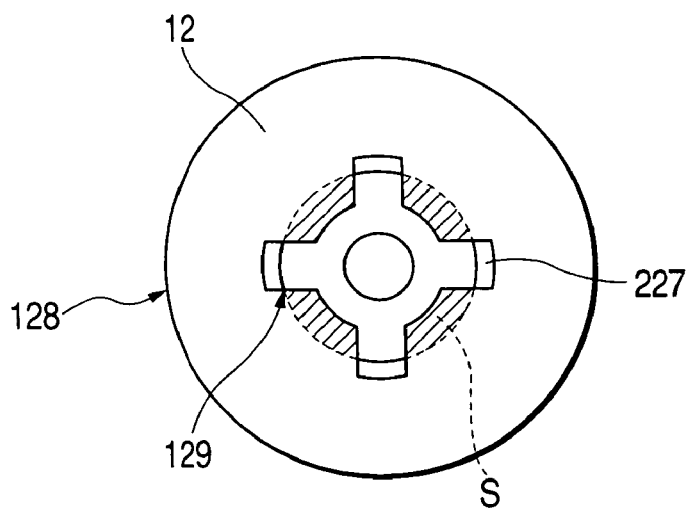
FIG. 7 is a horizontal sectional view as taken along the line D—D in FIG. 6.

The first insulation porcelain 12 has formed therein, as clearly shown in FIG. 7, a cylindrical bore in which four grooves are formed radially at regular intervals. The first insulation porcelain 12 is placed at a lower end thereof, as viewed in FIG. 6, on an upper end, as indicated by hatched lines S in FIG. 7, of the solid electrolyte body 30. Within spaces 227 defined between the grooves and the outer wall of the first insulation porcelain 12, metal terminal plates 213 and 214 are disposed which connect the measuring and reference gas electrodes of the sensor element 3 and the connectors 189. Other arrangements are identical with those in the one shown in FIG. 1, and explanation thereof in detail will be omitted here.

The assembling of the gas sensor 1 is accomplished in the following steps.

First, the protective cover assembly 191 is fitted at an end thereof in an annular groove formed in the end of the housing 19 and fixed by staking a peripheral wall extension formed around the groove. The peripheral wall extension is then welded to the end of the protective cover assembly 191. The heater 35 is fitted in the solid electrolyte body 30 of the sensor element 3. The metal terminal plates 213 and 214 are installed on the solid electrolyte body 30.

Next, the sensor element 3 is built in the first insulation porcelain 12. The leads 180 are coupled with the metal terminal plates 213 and 214 through the connectors 189. The elastic ring 13 is placed on the first insulation porcelain 12. The air cover 10 is fitted on the first insulation porcelain 12.

Figure 8:
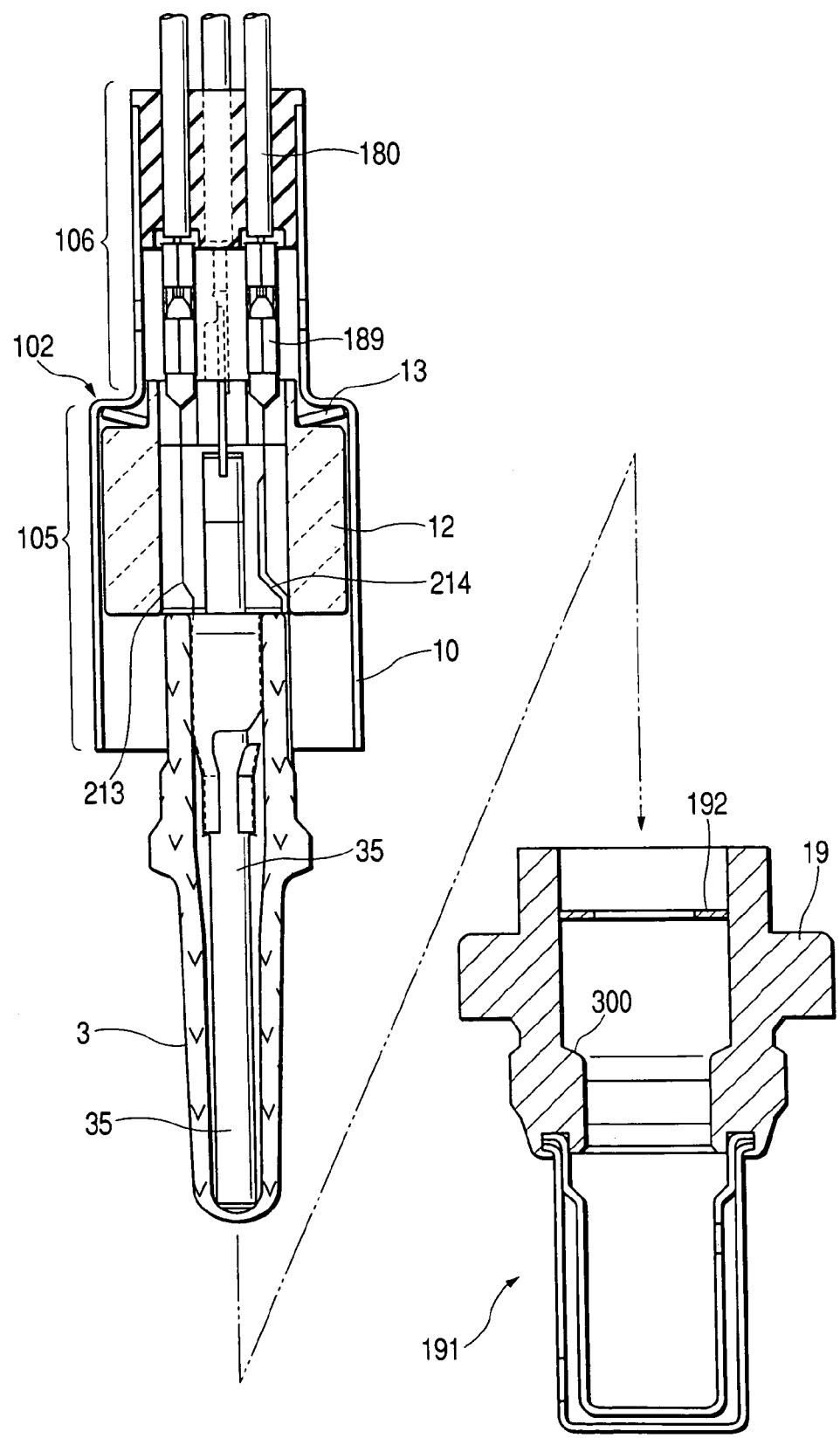
FIG. 8 is a sectional view which shows the process of inserting a sensor element into a housing to form a sensor assembly.

The metallic packing ring 192 is, as clearly shown in FIG. 8, put in the housing 19 and placed on the annular shoulder 300 formed on the inner wall of the housing 19. The air cover 10 is fitted on the first insulation porcelain 12 to form the assembly 100, as shown in FIG. 9.

Figure 9:
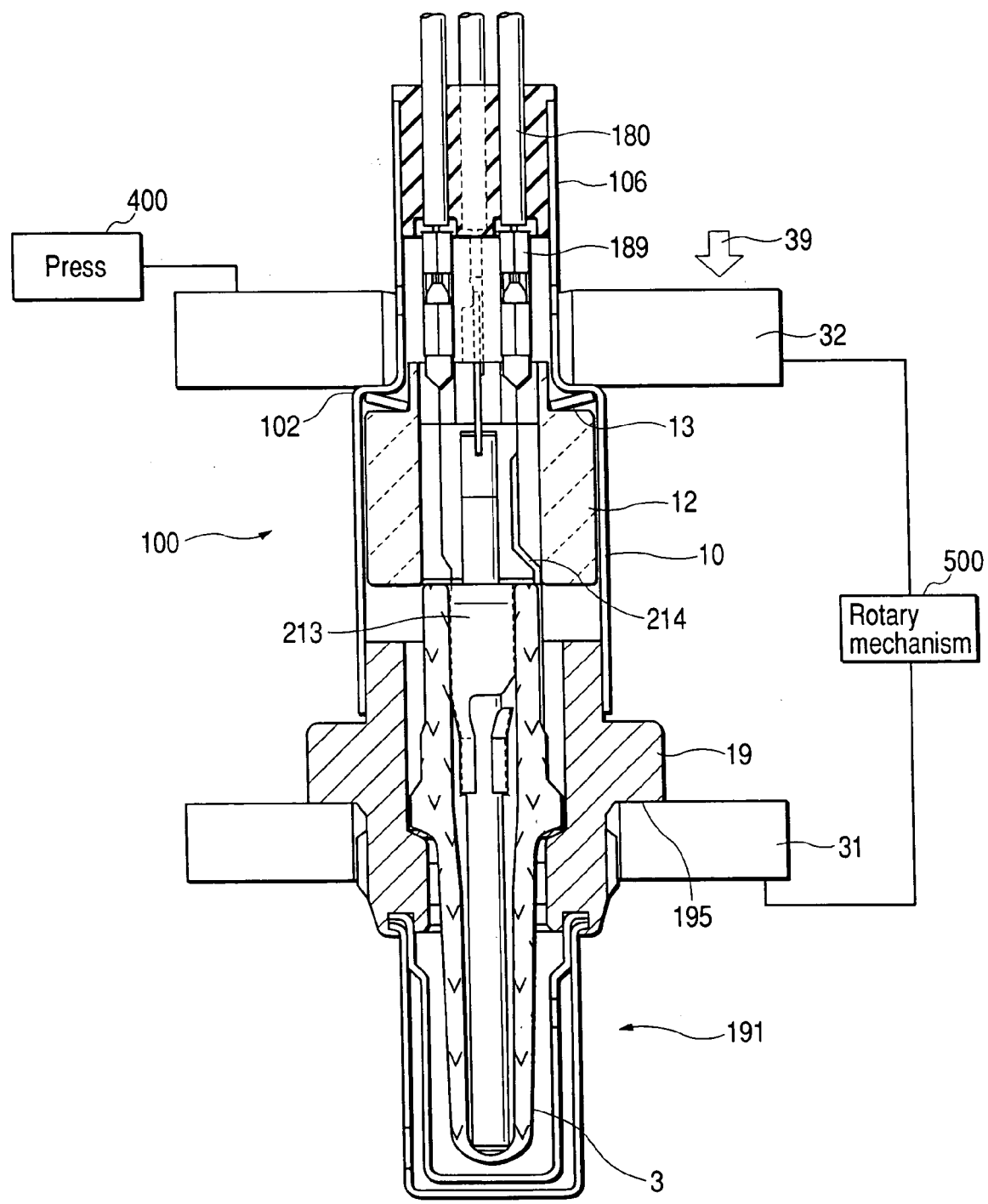
FIG. 9 is a sectional view which shows the process of pressing the sensor assembly of FIG. 8 for welding an air cover to a housing securely.

After the assembly 100 is prepared, the annular head plate 31 is, as shown in FIG. 9, fitted on the head of the housing 19 into contact with an end wall 195 of the flange 190 and then retained firmly in the manufacturing machine. Next, the annular base plate 32 is fitted on the small-diameter portion 106 of the air cover 10 and moved downward to fit the end of the air cover 10 on the base end portion of the housing 19.

Next, the end of the air cover 10 is welded to the base end portion of the housing 19 in the same manner as one of the above described first to third embodiment.

Other assembling steps are identical with those in the first embodiment, and explanation thereof in detail will be omitted here.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas sensor manufacturing method comprising the steps of: preparing an assembly which has a length and includes (a) a housing which has a length made up of a first end portion, a second end portion, and a flange between the first and second end portions, (b) a cover which is made up of a small-diameter portion, a large-diameter portion, and a shoulder formed between the small-diameter portion and the large-diameter portion, (c) a first insulation porcelain disposed in the large-diameter portion of the cover in contact with the shoulder through an elastic member, (d) a second insulation porcelain disposed in the housing in contact of an end thereof with an end of the first insulation porcelain in alignment with each other, and (e) a laminated sensor element disposed in the second insulation porcelain;

preparing a first press member to be stationary which retains the second end portion of the housing firmly;

moving a second press member at a first speed into abutment with the shoulder of the cover;

decreasing a speed of movement of the second press member after the abutment of the second press member with the shoulder of the cover and moving the second press member at a second speed, lower than the first speed, to press the cover against the housing in a lengthwise direction of said assembly until a given pressure is exerted on the shoulder to deform the elastic member and to fit an end of the large-diameter portion of the cover on the first end portion of the housing to form an overlap; and welding the large-diameter portion of the cover to the first end portion of the housing at the overlap while pressing the cover against the housing.

2. The gas sensor manufacturing method as set forth in claim 1, wherein said pressing step presses the cover against the housing while compressing the elastic member to urge the second insulation porcelain against an inner wall of the housing elastically to establish a hermetic seal between an outer wall of the second insulation porcelain and the inner wall of the housing.

3. The gas sensor manufacturing method as set forth in claim 1, wherein said welding step is performed while rotating the cover and the housing.

4. The gas sensor manufacturing method as set forth in claim 1, wherein said welding step is performed while fixing the cover and the housing.

5. The gas sensor manufacturing method as set forth in claim 1, wherein said welding step welds the large-diameter portion of the cover to the first end portion of the housing around an overall periphery of the overlap.

6. The gas sensor manufacturing method as set forth in claim 5, wherein said welding step welds the large-diameter portion of the cover to the first end portion of the housing around an overall periphery of the overlap through laser welding.

* * * * *